United States Patent [19]
Gibbons

[11] 3,930,496
[45] Jan. 6, 1976

[54] CAST FOR BROKEN LIMBS AND METHOD

[76] Inventor: Delamar J. Gibbons, P.O. Box 404, Blanding, Utah 84511

[22] Filed: Nov. 13, 1974

[21] Appl. No.: 520,520

[52] U.S. Cl................................. 128/90; 128/DIG. 20
[51] Int. Cl.²............................................ A61F 5/04
[58] Field of Search............ 128/91, 90, 89, 87, 595, 128/DIG. 20

[56] References Cited
UNITED STATES PATENTS

| | | | |
|---|---|---|---|
| 3,373,741 | 3/1968 | Hill et al. | 128/90 |
| 3,631,854 | 1/1972 | Fryer | 128/90 |
| 3,643,656 | 2/1972 | Young et al. | 128/90 |
| 3,656,475 | 4/1972 | Hanrahan, Jr. | 128/90 |
| 3,674,021 | 7/1972 | Snyder et al. | 128/90 |

*Primary Examiner*—John D. Yasko
*Attorney, Agent, or Firm*—Lynn G. Foster

[57] ABSTRACT

A cast for broken limbs and related method, the cast comprising a cylindrical, double wall sleeve fabricated of a thin polymeric or elastomeric material and containing a cylindrical batt of fiberglas or like reinforcement impregnated with a polymeric catalyst. The opposed ends of the cast are constructed so that the spaced sleeves are sealed one to another and also to the cylindrical batt of the fiberglas or the like, which is concentrically disposed within the cast intermediate the spaced sleeves. Spacers may be used to maintain said concentric relationship. The cast comprises a plurality of breather ports, the edges of which are sealed as are the ends of the cast. When it is desired to use the cast, a suitable polymeric material is injected through a filler port into the interior of the cast between the two spaced concentric sleeves. The physician manually kneads the resin within the cast causing the catalyst initially contained within the central reinforcement to become mixed into the polymer thereby initiating polymerization. The filling vessel is detached and the cast is placed upon the injured limb of the patient. A conventional wrapping, such as an elastic roll bandage, is placed on the cast to exert pressure causing the same to conform precisely to the exterior surface of the injured limb. The wrapping is removed once the resin has set and adequately cured.

9 Claims, 7 Drawing Figures

U.S. Patent　Jan. 6, 1976　Sheet 1 of 2　3,930,496
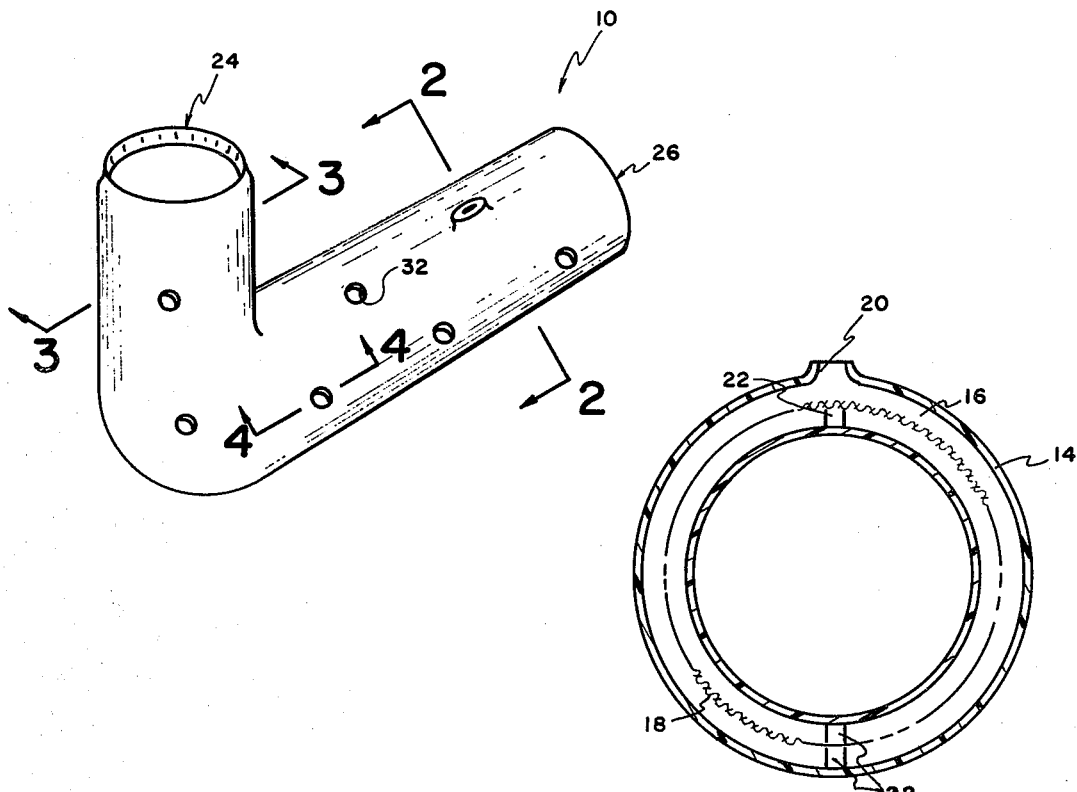
FIG. 1
FIG. 2
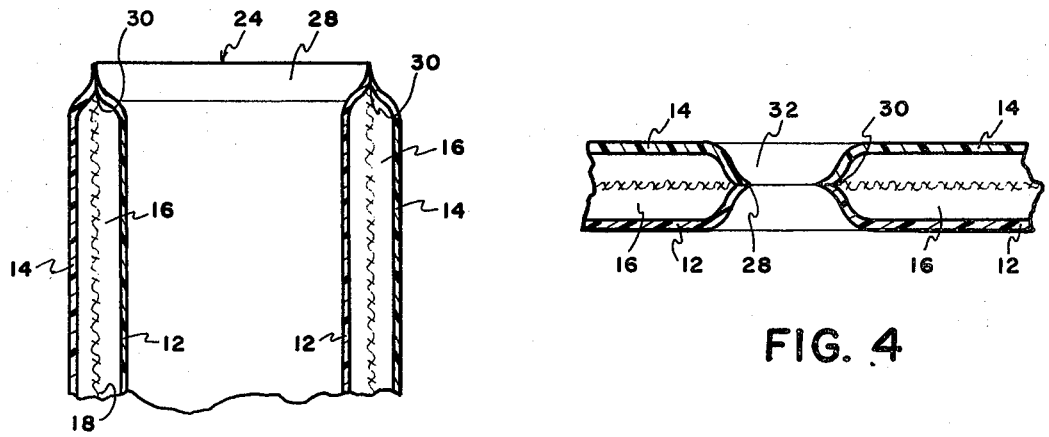
FIG. 3
FIG. 4

CAST FOR BROKEN LIMBS AND METHOD

BACKGROUND

1. Field of Invention

The present invention relates broadly to the art of placing a cast on an injured limb and more particularly to a novel cast comprising a pair of concentric sleeves sealed at the ends and containing therebetween a cylindrical batt of reinforcement impregnated with a resin activating substance which initiates polymerization when comingled with a suitable polymer, and a related method.

2. Prior Art

Heretofore, the use of a cast comprising plastic interior and exterior walls have most frequently utilized a polymeric foam in the interior between the sleeves. This has created a number of problems because it is difficult to control the foam and often the cast becomes a pressure-applying device rather than an instrument which restrains undesired movement of the limb. Also, such an approach prevents adequate breathing of the skin in the vicinity of the cast. As a consequence, the medical profession has used only to a limited extent such an approach.

BRIEF SUMMARY AND OBJECTS OF THE PRESENT INVENTION

With the foregoing in mind, it is a primary object of the present invention to provide a novel cast for injured limbs and related methods.

Another paramount object of the present invention is the provision of a novel cast wherein the cast comprises spaced concentric sleeves sealed one to the other at opposed ends and containing therein a cylindrical batt of reinforcement impregnated with a catalyst wherein a polymeric material is injected between the sleeves into contiguous relation with the reinforcement and is caused to be polymerized when mixed with the catalyst.

It is a further object of the present invention to provide a novel cast comprising a plurality of breather holes intermediate spaced cylindrical walls of the cast.

These and other objects and features of the present invention will be apparent from the following detailed description, taken with reference to the accompanying drawing(s).

BRIEF DESCRIPTION OF THE DRAWINGS

FIG. 1 is a perspective representation of one presently preferred cast embodiment in accordance with the present invention;

FIG. 2 is a cross section taken along lines 2—2 of FIG. 1;

FIG. 3 is a fragmentary cross section taken along lines 3—3 of FIG. 1;

FIG. 4 is a fragmentary cross section taken along lines 4—4 of FIG. 1;

DETAILED DESCRIPTION OF THE ILLUSTRATED EMBODIMENT

Figure 5:
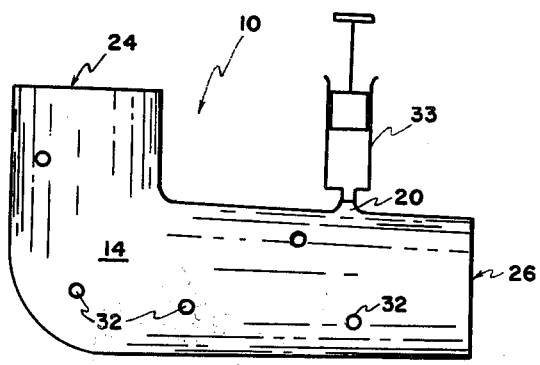
FIGS. 5—7 are line drawings illustrating the manner in which the cast of FIG. 1 is utilized.

Reference is now made to the drawings wherein like numerals are used to designate like parts throughout. FIG. 1 in particular illustrates a presently preferred embodiment in accordance with the present invention comprising a cast, generally designated 10, which consists of an interior elastomeric sleeve 12, preferably in the nature of a thin wall membrane of pliant synthetic resinous material, and an exterior sleeve 14 also preferably of a thin walled membrane of resinous material. Said sleeves 12 and 14 are generally concentric one within the other and together define a space 16 therebetween. Disposed in said space 16 in generally concentric relation intermediate sleeves 12 and 14 is a cylindrical batt 18 of porous reinforcing material which is impregnated with a suitable catalyst (resin activating substance) the function of which is to cause polymerization of a synthetic resin when the resin is inserted into the space 16 through 1 or more filler ports 20 formed in the exterior sleeve 14. A plurality of spacer studs 22 may be utilized to maintain the generally concentric relationship of the sleeves 12 and 14 and the cylindrical reinforcing batt 18. The spacer studs 22 are each preferably integral with the adjacent sleeve 12 or 14. It is preferred that the material of the batt 18 be fiberglas, although other types of reinforcement may be utilized.

The opposed ends 24 and 26 of the cast 10 are sealed, i.e. the inside and outside membrane walls 12 and 14 are heat sealed or resin bonded together along a lip 28 (FIG. 3) with the porous cylindrical batt 18 also being secured to said opposed sleeve ends at location 30 adjacent the seam 28. Thus, the interior 16 between the sleeves 12 and 14 is entirely sealed to the exterior atmosphere except at each filler port 20.

The cast 10 is provided with a plurality of breather ports 32, one of which is illustrated in FIG. 4. Each filler port 32 is sealed as is each end 24 and 26.

Figure 6:
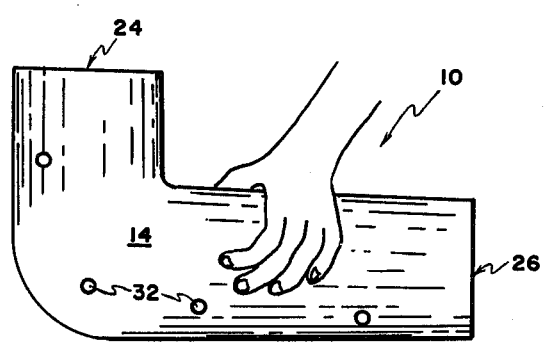
Figure 7:
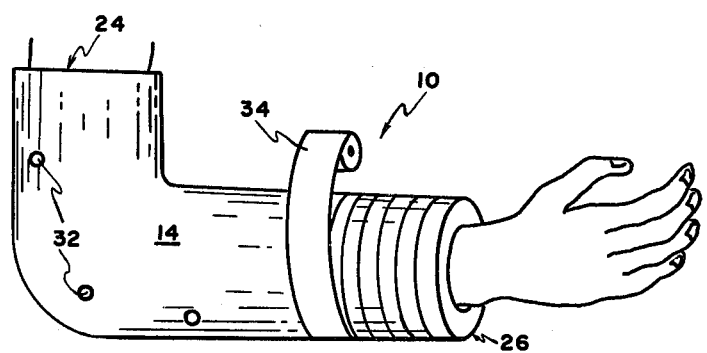

In the use, a suitable instrument such as a syringe 33 containing a satisfactory resinous material is united with a filler port 20 and the resinous material injected through the filler port 20 into the space 16 between the sleeves 12 and 14 (See FIG. 5). Air contained within the space 16 is preferably evacuated during injection of the resin through a second filler port 20. Once a suitable quantity of desired resin has been injected into the space 16, the resin is kneaded by the physician, nurse or the like through the exterior sleeve 14 (FIG. 6). Once the resinous material has been adequately kneaded so as to mix in a reasonably homogenous manner the resin with the catalyst or activator, the cast, while still pliable is placed upon the injured limb of the patient and is wrapped with a suitable wrapping 34, which may be an elastic roll bandage. This step causes the cast to conform to the exterior surface of the injured limb without applying unneeded and undesired exterior pressure. Once the resin has set and adequately cured, the wrapping 34 is removed. A very strong, somewhat resilient cast results which is ideally suited for injured limbs.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. A cast for injured limbs comprising:
    spaced generally concentric elongated sleeves, the axis of which is parallel to the limb of the patient upon which it is to be used, of pliant impervious resinous material defining a hollow space between the sleeves;

porous reinforcing material disposed within said space and comprising the only substance between the sleeves, said reinforcing material carrying a resin activating substance;

at least one resin ingress port in the outer sleeve whereby inactive resin is injected into said space and caused to be activated and polymerized by intermingling the inactive resin with said activating substance to ultimately form a resilient shape-retaining cast the exterior of which comprises said sleeve and the interior of which consists of polymerized resin and said reinforcing material.

2. A cast according to claim 1 further comprising means sealing opposed ends of the cast intermediate the concentric sleeves.

3. A cast according to claim 1 wherein said porous reinforcing material comprises a batt of fibers initially cylindrically generally concentrically disposed within the space between said sleeves.

4. A cast according to claim 3 wherein the initial generally concentric relationship between the sleeves and the batt of reinforcement is achieved by spacers.

5. A cast according to claim 1 further comprising skin breather ports for aerating the skin of the patient disposed between the ends of said cast and spanning transversely through and between both sleeves and means sealing said sleeves one to another at each said skin breather port.

6. A method of placing a cast upon an injured limb comprising the steps of:

providing a pair of generally concentric elongated sleeves secured one to the other at opposed ends, the sleeves comprising pliant impervious resinous material whereby a space is defined between the concentric sleeves the axis of which is essentially coextensive with the limb of the patient upon which it is placed, the space having porous reinforcing material only disposed therein which carries a resin activating substance;

displacing inactive resin through an ingress port in the outer sleeve and a portion thereof across the porous reinforcing material into contiguous relation with the inside sleeve to substantially fill the space between said sleeves;

manually causing intermingling between said displaced inactive resin and said activating substance to cause activation and initiate polymerization of the resin within the space between said sleeves;

axial displacing the resin filled sleeves upon the injured limb during polymerization before the resin has set;

thereafter applying external pressure to the resin filled sleeves upon the injured limb to bring the cast into contiguous conformity with the exterior of the injured limb and retaining said pressure until the resin within the sleeve has adequately set and cured so as to constitute a resilient shape retaining cast; and removing said pressure.

7. A method according to claim 6 wherein said resin displacing step comprises injecting the resin through a filler port in the outer sleeve.

8. A method according to claim 6 wherein said external pressure is applied by wrapping the cast with a yieldable bandage to cause said contiguous conformity.

9. A method according to claim 6 wherein said intermingling step comprises manually kneading the cast through the outer sleeve.

* * * * *